(12) United States Patent
Liebler et al.

(10) Patent No.: US 6,379,970 B1
(45) Date of Patent: Apr. 30, 2002

(54) ANALYSIS OF DIFFERENTIAL PROTEIN EXPRESSION

(75) Inventors: Daniel C. Liebler; Thomas D. McClure; Garth Powis, all of Tucson, AZ (US)

(73) Assignee: The Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 09/302,475

(22) Filed: Apr. 30, 1999

(51) Int. Cl.[7] .......................... G01N 33/00; C12Q 1/68
(52) U.S. Cl. ..................... 436/86; 436/89; 436/16; 435/6; 435/267; 435/272; 435/804; 536/18.7; 536/22.1; 536/23.1; 536/24.3; 536/24.31; 536/24.32; 536/25.32; 536/25.4; 536/25.41; 536/26.6; 204/451; 204/601; 204/459; 204/610
(58) Field of Search ...................... 436/16, 86, 89; 435/6, 267, 272, 804; 536/18.7, 22.1, 23.1, 24.3, 24.31, 24.32, 25.32, 25.4, 25.41, 26.6; 204/451, 601, 459, 610

(56) References Cited

U.S. PATENT DOCUMENTS

| | | | | |
|---|---|---|---|---|
| 4,725,536 A | * | 2/1988 | Fritsch et al. | 435/6 |
| 5,643,722 A | | 7/1997 | Rothschild et al. | |
| 5,747,269 A | * | 5/1998 | Rammensee et al. | 435/7.24 |
| 5,858,683 A | * | 1/1999 | Keesee et al. | 435/7.1 |
| 5,885,841 A | * | 3/1999 | Higgs, Jr. et al. | 436/89 |
| 5,972,692 A | * | 10/1999 | Hashimoto et al. | 435/285.2 |
| 6,027,890 A | * | 2/2000 | Ness et al. | 435/6 |
| 6,054,266 A | | 4/2000 | Kronick et al. | |
| 6,064,754 A | | 5/2000 | Parekh et al. | |
| 6,177,247 B1 | * | 1/2001 | Mathies et al. | 435/6 |

* cited by examiner

Primary Examiner—Jill Warden
Assistant Examiner—Monique T. Cole
(74) Attorney, Agent, or Firm—Oblon, Spivak, McClelland, Maier & Neustadt, P.C.

(57) ABSTRACT

A method of detecting peptide fragments of protein(s) that are differentially present in biological samples. The identity of the peptides may be determined and correlated with the protein(s) that are differentially present in the samples.

22 Claims, 2 Drawing Sheets

ANALYSIS OF DIFFERENTIAL PROTEIN EXPRESSION

BACKGROUND OF THE INVENTION

1. Field of the Invention

The present invention relates to a method of identifying proteins which are differentially expressed in a plurality of biological samples. An important component of the inventive method is digesting the proteins contained in the samples to produce peptides, followed by labeling of the peptides. The labeled peptides are then separated, and those peptides that are differentially present in the samples are identified. The identity of the peptides that are differentially present in the samples may be used to determine which protein(s) in the original biological samples were differentially expressed.

2. Background of the Invention

Of the many genes in the genome, some are expressed in virtually all cells, whereas others are expressed in cell- and tissue-specific patterns. Cancer cells express different genes as compared to normal cells. These genes encode proteins that, in turn, regulate all aspects of cell function, including those that give rise to neoplastic characteristics. In principle, analyses of expressed genes in tumor cells versus normal cells should indicate which genes and gene products are characteristic of the neoplastic phenotype. DNA microarrays and related techniques have revolutionized the approach to this problem. Indeed, this approach is expected to yield profound insights into not only into the induction of neoplasia, but also the responses of neoplastic cells to therapeutic agents. Nevertheless, the correspondence between what genes are expressed and what proteins are produced is uncertain. Recent studies indicate that the correlation between mRNA induction and elevation in protein content for several enzymes is relatively poor. Variations in protein expression may be due not only to variations in gene expression, but also to variability in mRNA stability, translational efficiency, protein stability and turnover. Thus, analyzes of genomic expression patterns will not necessarily provide an accurate picture of the status of the truly functional cellular machinery—the proteins.

The term proteome was introduced by Wilkins and colleagues to describe the protein complement of the genome. It is estimated that human cells contain between 50,000 and 100,000 expressed proteins. Proteomics has emerged as a buzzword complement to genomics. Proteomics describes the study of the proteome and changes in its status. In its simplest form, proteomics is simply an exercise in "mining" samples to identify the proteins present. However, the main attraction of applied proteomics in cancer research is that it can reveal key differences between the proteomes of normal and neoplastic cells. In addition, applied proteomics will reveal unique proteins or protein expression patterns of neoplastic cells, both of which can serve the task of molecular diagnosis of cancer.

Previous work describing changes in the expression of single genes or changes in the status of single proteins provided very specific information that could be interpreted in a limited biochemical context. Although the impact of many specific changes in gene and protein regulation is understood, we now realize that the factors regulating cell growth and differentiation act in complex, interlocking pathways. Accordingly, changes in biochemical signaling pathways, networks, and regulatory cascades, rather than in single enzymes describe how cells grow, differentiate and die. By collectively describing complex, multicomponent systems, both genomics and proteomics promise a quantum leap in our level of understanding of the biology of cancer. A crucial task of the new biology is to make mechanistic sense of these changes. First, however, it is necessary to reliably detect and describe them. DNA microarray techniques now make this possible in the context of gene expression. However, no equivalent methodology yet exists to reliably compare, characterize and define patterns of protein expression between cells and tissues.

Investigators studying proteomics are at an enormous disadvantage compared to their genome scientist colleagues. First, unlike nucleic acids, proteins do not hybridize to complementary sequences. Second, there is no protein equivalent of the polymerase chain reaction (PCR). Proteomics thus requires other means of separating proteins in complex mixtures and identifying both low-and high-abundance species. The most powerful method currently available to resolve complex protein mixtures is 2D gel electrophoresis. In this technique, proteins are resolved on the basis of some physical property (e.g., isoelectric point) in a first dimension separation, and then by molecular weight in the second dimension. Many individual proteins from complex cell extracts can be resolved on 2D gels. Although 2D gels are currently the most widely used separation tool in proteomics, it is worth noting that reverse phase HPLC, capillary electrophoresis, isoelectric focusing and related hybrid techniques also provide powerful means of resolving complex protein mixtures.

Regardless of the means by which they are resolved, proteins must next be identified, primarily on the basis of sequence information. N-terminal Edman sequencing provides useful information in many cases, except where N-terminal modifications block analysis. The state-of-the-art approach to protein identification is mass spectrometry (MS). Spots containing the proteins of interest typically are excised from gels and subjected to proteolytic digestion. The resulting peptides may be analyzed by electrospray (ESI) or matrix-assisted laser desorption ionization (MALDI) MS. Sequence information is obtained with triple quadruple or ion trap mass analyzers by collision induced dissociation (CID) or on time of flight (TOF) mass analyzers by post-source decay. In either case, the ability of MS instruments to perform MS-MS experiments allows unambiguous assignment of peptide sequence. This information then may be used with sophisticated database search programs, such as SEQUEST, to identify proteins in World Wide Web protein and nucleic acid databases from the MS-MS spectra of their peptides. This combination of separation technology, MS analysis, and database searching makes the high-throughput identification of proteins in complex mixtures possible and has been the driving force behind the recent explosive growth of the proteomics field. With the continued growth of databases, it will possible to identify virtually all proteins from any 2D gel with these approaches. Indeed, investigators studying proteins of S. cerviseae, in which the entire genome has been sequenced, have made excellent progress in characterizing the yeast proteome.

With few exceptions, 2D gel approaches dominate the proteomics field today. Not surprisingly, a great deal of effort has been directed at overcoming the major technical limitations of 2D gel electrophoresis. Briefly, these limitations are:

(1) difficulties in solubilizing and achieving isoelectric focusing (i.e. 1st dimension) separations with proteins of a wide range of isoelectric points and solubility, (2) difficulties in achieving run-to-run and laboratory-to-laboratory reproducibility in 2D gel profiles, (3) problems in resolving the many proteins typically present in the 30–100 kDa MW range, and (4) difficulty in detecting low abundance proteins.

While progress has been made in addressing all of these problems, 2D gel technology is ultimately limited by the diversity of proteins to be analyzed, both in physical properties and abundance. Continued improvements certainly can be expected, but the 2D gel approach for proteins will ultimately prove inadequate to the demands of proteomics.

Accordingly, there remains a need for improved methods of assaying for differential expression of proteins in biological samples.

SUMMARY OF THE INVENTION

It is an object of the present invention to provide a method to identify proteins that are differentially expressed in different biological samples, e.g., cell or tissue samples.

It is another object of the invention to provide a method to identify peptides derived from proteins which are differentially expressed in different biological samples.

The present invention exploits the fact that relatively short peptide sequences (e.g., 6-mer or larger; equivalent to an 18-mer oligo) are largely unique in proteins. This means that sequence identification of one or more such peptides in a protein digest is sufficient to establish the presence of the precursor protein in a sample with a high degree of confidence. Thus, if one identifies, for example, an 8-mer peptide, a search of a protein or nucleotide sequence database will permit the sequence to be localized to a specific protein.

The present invention is based, in part, on detecting the differential expression of the same protein in two examples, or the presence of protein(s) in some, but not all, samples by analysis of peptide fragments from each sample. To that end, the method of the present invention includes digesting the proteins in two samples to a mixture of peptides and then comparing the abundances of specific peptides. A protein that is abundantly expressed in one sample will give rise to greater amounts of product peptides upon digestion than the same protein expressed in another sample at trace amounts. Thus, the task of identifying differentially expressed proteins between two samples involves 1) digestion of two samples, 2) detection and selection of peptides that are present in different amounts in the two samples, and 3) sequence analysis of the selected peptides and identification of the protein precursors.

The objects of the present invention, and others, may be accomplished with a method of detecting peptide fragments of protein(s) that are differentially present in biological samples, by digesting the proteins in a plurality of biological samples to produce peptides in each sample;

separating the peptides in the samples; and identifying the peptides that are differentially present in the samples.

The objects of the present invention, and others, may also be accomplished with a method of identifying protein(s) that are differentially present in biological samples, by detecting peptide fragments of protein(s) that are differentially present in biological samples as described above;

determining the amino acid sequence of at least a portion of the peptide fragments; and correlating the amino acid sequences of the peptide fragments with the identity of the protein(s) that are differentially present in the samples.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
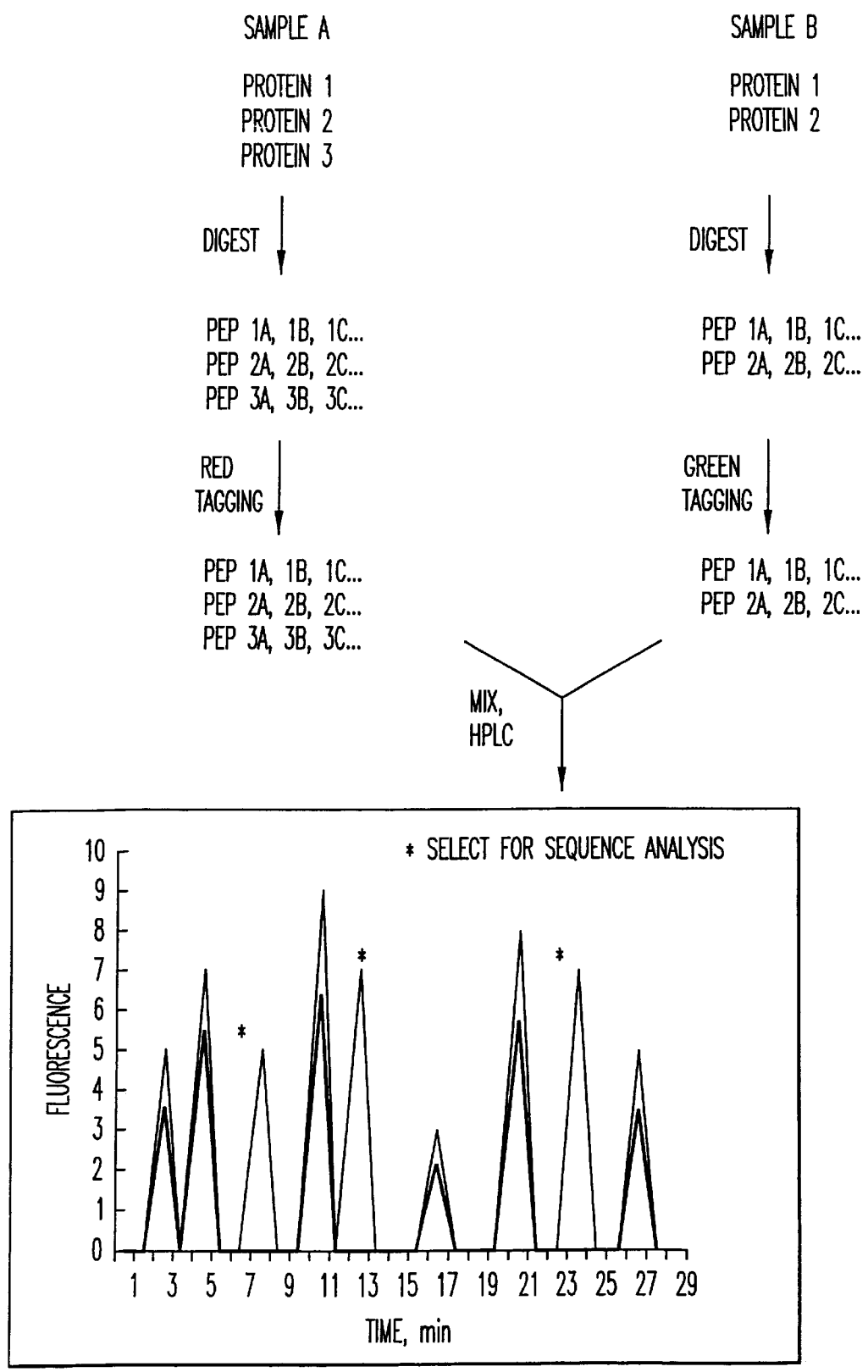
FIG. 1 is a schematic representation of method for selective detection of peptides from differentially expressed proteins.

The present invention provides a method of identifying protein(s), i.e., one protein or more than one protein, that are differentially present in samples. When the sample is a biological specimen, the information provided by the inventive method may be used to determine which protein(s) were differentially expressed in the original sample. As used herein, the term "differentially present" means that one or more proteins is present at a higher relative amount in a portion of the samples as compared to the remainder of the samples. The term also means that protein(s) are present in a portion of the samples that are not present in the remainder of the samples. Of course, it may be the case that protein(s) are present at a higher relative amount in a portion of the samples as compared to the remainder of the samples and protein(s) are present in a portion of the samples that are not present in the remainder of the samples.

One non-limiting, embodiment of the present invention involves the analysis of two peptide mixtures together in one analytical run. Use of differential labeling for the two samples yields one sample peptide mixture with a characteristic (e.g., red) label, whereas the peptides in the other sample mixture bear a different characteristic label (e.g., green). Once the mixtures are combined and then subjected to some analytical separation, variations in the ratio of signals from the two labels (i.e., a change in the red:green ratio) indicates different amounts of that particular peptide, and, thus, differential expression of the precursor protein. These peptide pairs are then selected for further analysis by LC-MS.

Biological Samples

The nature of the biological samples is not limited, provided that the samples contain proteins. The sample may contain whole cells or ruptured cells. The biological sample may be a blood sample, a biopsy sample. Samples containing whole cells may be processed to isolate the proteins, i.e., to separate the cellular proteins from the other cellular components, using any of the techniques that are well-known in the field of biological and diagnostic assays.

Samples may comprise cultured cells or cultured organ specimens, tissues taken from biopsy or dissection procedures, or blood or other biological fluids. One of the most important aspects of applying the inventive method to cellular systems is to reproducibly extract cellular proteins from the cell samples being compared. A failure to reproducibly extract proteins in the two samples could either mask real differences in expression or suggest false differences. Extractions are based on the methods outlined in a recent review, which entails 1) the use of DNase and RNase to degrade nucleic acids, 2) an anionic detergent (e.g., CHAPS), and 3) a reductant (e.g., DTT or b-mercaptoethanol), see Walsh et al, ABRFnews 9, pp. 11–21, 1998, incorporated herein by reference. Other adjuncts to improve protein solubility or isoelectric focusing separation in 2D SDS-PAGE include SDS and ampholytes. Adaptation of extraction methods to individual samples is largely empirical, but can be based on known methods to prepare protein samples for 2D SDS-PAGE, see Link et al, Electrophoresis 18, pp. 1314–1334, 1998; and Ducret et al, Protein Sci. 7, pp. 706–719, 1998, both of which are incorporated herein by reference.

In principle, there is no limit on the number of samples that may be analyzed. However, the number of samples is preferably 2 to 100, more preferably 2 to 25, even more preferably 2 to 10. Analysis of 2 samples is a particularly preferred embodiment of the present invention.

Protein Digestion

The proteins contained in the biological samples may be digested with any of the well-known protein digestion reagents. Such reagents may be chemical or enzymatic. Preferably, the N-termini of the peptide fragments are free, i.e, the N-terminal end of each peptide is a free amino group. In this case, the free amino groups serve as a convenient location at which to label the peptides, as discussed below. A particularly preferred reagent for the protein digestion is cyanogen bromide (CNBr). As will be recognized by one skilled in the art, the conditions of the digest are adjusted such that peptides are produced which are amenable for separation, detection and identification.

For CNBr cleavage, the peptides may range in size from 1 amino acid to 20 or more, depending on the protein sequence. Thus, the molecular weight for such peptides is from 50 to 20,000 daltons. Unique sequences may lack methionine residues (where CNBr cleaves) for stretches of more than 20 amino acids, but this circumstance is rare. For a detailed description of protein digestion see *Protein Structure: Practical Approach*, T. E. Creighton, ed., ILR Press, 1989, pp 117–144, incorporated herein by reference.

Peptide Labeling

The peptides from the digests may be labeled by any of the well-known techniques available in the art. The label is preferably a chemical group that facilitates facile detection of the peptides.

The peptides may be labeled at any position in the amino acid sequence, such as at the N-termini, C-termini, or at an amino acid side chain (e.g., Lys, Arg, Ser, Cys, Tyr, Glu, Asp, etc.). However, since not all side chains will be present in all of the peptides produced in the digest, labeling at the N-, or C-termini is preferred. N-terminal peptide labeling is particularly preferred.

Figure 2:
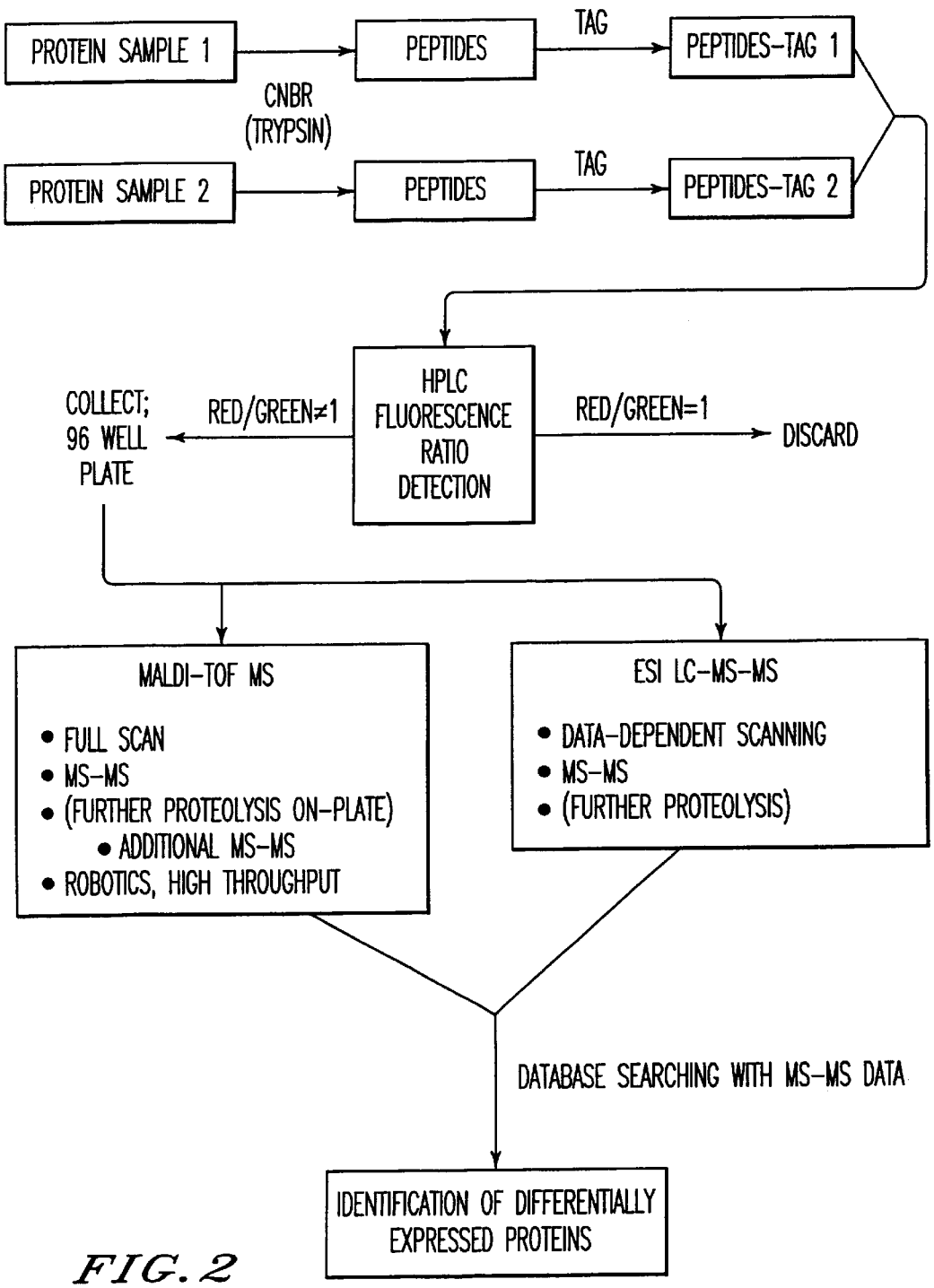
FIG. 2 is a schematic representation of method for identification of differentially expressed proteins.

Preferred labeling groups are fluorescent chromophores that are conventionally used as reporter groups. For example, the structurally related cyanine (Cy™) fluorescent labeling reagents, Cy3 and Cy5, may be used to produce N-terminally-tagged peptides (FIG. 2). These dyes have very similar structures, the only difference being the presence of an additional methylene group in the polyene linker chain in Cy5. Both dyes are intensely fluorescent and water soluble, which will facilitate their use in labeling peptide mixtures. Incubation of the Cy3 or Cy5 monofunctional succinimide esters with the peptide will result in N-terminal labeling of the peptides. These dyes are commercially available from Amersham Pharmacia Biotech.

Alexa™ dyes marketed by Molecular Probes, Inc. may also be used. These dyes comprise a series of fluorophores with emission maxima throughout the visible spectrum. Of these, two dyes, Alexa 532 and Alexa 568 would be especially suitable (FIG. 5). Both share a similar fluorophore and bear the same polar sulfonate and quaternary nitrogen functional groups in similar spatial orientation in the molecule. Their emission maxima are at 554 nm and 603 nm, respectively. Although these compounds are structurally related, they are not as closely matched in structure as are the Cy dyes discussed above. Therefore, the Cy dyes are preferred over the Alexa dyes.

In a preferred embodiment, the peptides in each biological sample are labeled with a different moiety that permits specific detection of the peptides from that sample. For example, in the case where two samples are analyzed, the peptides from the first sample are labeled with a red label and the peptides from the first sample are modified with a green label. In a most particularly preferred embodiment, the labels do not alter the detection of a particular peptide sequence that may be present in multiple samples. For example, in the case where two samples are analyzed, a peptide sequence modified with label (1) in sample 1 has the same detection signature (e.g., HPLC retention time, relative gel mobility) as the peptide modified with label (2) in sample 2.

Peptide Separation

A variety of techniques well-known for separating peptides may be used to separate and detect the labeled peptides. For example, peptides may be separated by a variety of techniques. Such techniques include 2D gel electrophoresis, capillary electrophoresis, isoelectric focusing and liquid chromatography. A preferred analytical method for separating the labeled peptides is high-performance liquid chromatography (HPLC). Reverse-phase HPLC is a routine analytical procedure in the field of protein and peptide analysis, and may be successfully used in the inventive method.

In reverse phase HPLC C-18 columns typically are used, although shorter-chain stationary phases provide improved resolution for larger polypeptides. Three column formats are most widely used. Analytical columns (4.6 mm I.D.) typically are eluted at flow rates of 0.5–2 mL min$^{-1}$. Narrow bore columns (1 mm I.D.) are run at approximately 0.1 mL min$^{-1}$. Fused silica capillary columns (0.1–0.3 mm I.D.) are eluted a flow rates of 4 $\mu$L min$^{-1}$ and below. There are three advantages conferred by microscale HPLC separations. First, resolution of individual peptide components is often improved relative to standard analytical columns. Second, narrow bore and capillary columns expose the sample to less total surface area in the column and result in lower loss of sample via nonspecific adherence. Finally, low flow rates lead to highest sensitivity in ESI-LC-MS analyses, which are used for in-line sequence analysis of peptides. Indeed, capillary LC-MS has become the method of choice for high sensitivity/high throughput sequence analysis of peptides in complex mixtures.

In a preferred embodiment, the samples containing the labeled peptides are combined prior to separation. In this embodiment, a single analytical step, e.g., a single HPLC separation, produces the data necessary to identify the differentially expressed proteins in the original samples.

Identification of Peptides

An further aspect of the inventive method is identifying the peptides which are produced from proteins in the original samples that are differentially expressed. This portion of the method involves identifying peptides that are present in some, but not all, of the original samples, i.e., identifying the peptides that are present in only a portion of the original samples. For example, when a protein is present in one sample, sample 1, but not any of the other samples, separation of all of the peptides in each sample as described above will reveal that the sample 1 contains peptides that are not present in any of the other samples. These peptides are referred to as the "signature peptides". The signature peptides are derived from the protein or proteins that were present in sample 1 but not sample 2.

In an embodiment where the labeled peptides from each sample are not combined, the signature peptides can be detected by multichannel detection. For example, in an embodiment where two original biological samples are analyzed, each label may have a different wavelength where it can be specifically detected, e.g., the label in the first sample can be detected in the red region and the label in the first sample can be detected in the green region. The labels may simultaneously be monitored by a dual wavelength detector. This embodiment is shown in FIG. 1. In the Figure, the peptide separation reveals the presence of signature peptides in sample A (red label) at 8 and 13 and 24 minutes.

In order to ensure that differences in amounts of peptides reflects actual differences in protein expression, it is preferable to normalize the samples based on total protein content. In other words, the sample volumes are adjusted so that each sample has the same concentration of total protein.

A further embodiment of the present invention uses an HPLC analytical system that permits resolution of the peptide mixture while permitting co-elution of peptides differing only in their N-terminal labeling. The co-elution of differently labeled peptides is important for selecting peptides present at different levels based on the ratios of the two fluorescence signals. Reverse phase HPLC is the dominant approach to characterizing peptide mixtures. Separation of complex peptide mixtures may be conducted on standard, narrow bore, or capillary columns with a C-8 or C-18 stationary phase and a water/acetonitrile/trifluoroacetic acid mobile phase.

After identifying which peptides are signature peptides, the sequence thereof can be determined. Any of the well-known methods for determining the sequence of a peptide may be used. A particularly preferred method of peptide sequence analysis is MS. A variety of MS techniques are routinely used to determine peptide sequence. For example, MALDI-TOF MS or ESI MS may be used.

Two MS ionization methods used in the field of protein analysis are electrospray ionization (ESI) and matrix-assisted laser desorption ionization (MALDI). Both methods are effective means of producing gas phase ions of proteins, peptides and other biomolecules for MS analysis. ESI sources typically are used on quadrupole or ion trap mass analyzers, whereas MALDI sources are typically used with time-of-flight (TOF) mass analyzers. Although a variety of hybrid instruments have been produced. Both ESI and MALDI are capable of sub-femtomole sensitivity for peptide analysis. ESI-triple quadrupole or ESI-ion trap instruments can be used for MS-MS analyses that yield peptide sequence information. MALDI instruments equipped with post source decay capability also can generate peptide sequence information although ESI-triple quadrupole and ESI-ion trap instruments are considered the best for true MS-MS sequencing.

ESI and MALDI differ in the types of ions produced. ESI essentially samples peptide ions present in solution; thus acid-base equilibria generate singly and multiply charged ions. For larger peptides (>1000 MW) multiply charged ions usually predominate. A "multicharge envelope" is commonly seen with polypeptides>10,000 MW. Available algorithms permit deconvolution of multicharge envelopes to yield a derived spectrum indicating the molecular mass of the peptide. Algorithms are described in the following, each of which is incorporated herein by reference: Convey et al, Rapid Commun. Mass Spectrom. 2, p. 249; Loo et al, Anal. Biochem. 179, p.404; Mann et al, Anal. Chem. 61, p. 1702.; U.S. Pat. Nos. 5,844,237; 5,689,111; 5,652,427; 5,432,343.

An advantage of multicharging is that the multicharged ions fall within the mass range of quadrupole and ion trap mass analyzers (typically up to 2000–4000 Da). However, overlapping multicharge envelopes of protein/peptide mixtures generate a very complicated spectrum and can make this task very difficult. In contrast, MALDI produces primarily singly charged ions and no multicharge envelopes. TOF mass analyzers have greater mass ramps than quadrupoles and are capable of reasonably accurate mass measurements of singly charged ions up to 50 kDa or higher.

Advantages of the MALDI-TOF over the ESI triple quadrupole or ion trap instruments thus are:

(1) MALDI produces a simpler spectrum (i.e., single charging vs. multicharging) from complex samples. This facilitates rapid MS identification of the peptides of interest.

(2) TOF analyzers display a greater mass range than quadrupoles or ion traps, particularly for peptides that do not undergo significant multicharging. This may be important for some peptides with few basis sites for protonation, as the Cy dye labels occupy a protonation site and confer a net charge of minus one.

(3) MALDI-TOF: instruments offer a considerably greater speed of analysis and automation than HPLC-ESI-MS systems. The interface of the instrument with a robotic workstation automates proteolytic cleavage of the collected CNBr peptides and MS analysis of the peptide fragments.

A convenient way to perform the dual- (or multi-) channel detection is to monitor the ratio of the absorbances at the specified detection wavelengths. A deviation of the ratio from unity indicates that a signature peptide is eluting from the detector. At this point, the eluate can be transferred to a suitable storage container, e.g., a vial or a 96 well assay plate, for further analysis.

Accordingly, the signature peptides may be isolated after the separation. The isolated peptides may be further purified, if desired.

Correlation of Differentially Produced Peptides with Differentially Expressed Proteins Using the amino acid sequences of the signature peptides, determined as described above, the identity of the protein(s) that are differentially expressed in the original samples may be determined. To do so, the amino acid sequences of the signature peptides may be used to search a database of protein sequences. This search would reveal the amino acid sequences of known protein(s) which contain the peptide sequences as subsequences therein. This analysis may reveal that one, or more than one, protein was differentially expressed in one of the original samples.

The sequence database may be a protein or a nucleic acid sequence database. As will be recognized by those skilled in the art, a nucleic acid sequence database may be searched by using the standard genetic code to determine the possible nucleic acid sequences which encode the signature peptides.

Several databases in FASTA (ASCII text) format with protein sequence information can be accessed with standard web-browsing software over the world wide web (WWW). These include, for example, the SWISS-PROT database (http:/www.expasy.ch/sprot/) and OWL database (http;/www.biochem.ucl.ac.uk/bsm/dbbrowser/OWL/OWL.html). Nucleotide sequence databases contain sequences for expressed sequence tags (ESTs), which correspond to expressed genes and gene fragments. EST sequence databases, such as the ESTdb at the National Center for Biotechnology Information (http:/www.ncbi.nlm.nih.gov/dbEST/index.html) can be accessed in the same manner as protein sequence databases.

Isolation of Genes Coding for Differentially Expressed Proteins

The amino acid sequences of the signature peptides may be used to isolate nucleic acids which encode proteins having the peptide sequences as subsequences therein. This aspect of the present invention is particularly useful when the database search of protein sequences, described above, fails to identify a protein from which the peptide was derived by digestion. Such a result may indicate that an unknown, differentially expressed protein is present in the sample.

Using amino acid sequence of the signature peptides and the genetic code, if oligonucleotide primers may be constructed that are capable of hybridizing to a nucleic acid sequence encoding the peptide sequence. The probes may be based on a sub-fragment of the sequence of a signature peptide. Hybridizing is preferably conducted under stringent conditions, which are well-known in the art. The primers can be contacted with nucleic acid obtained from the original biological samples in order to identify which nucleic acids encode the peptide, or sub-fragment thereof. Using standard techniques, such nucleic acids can then be isolated and sequenced in order to reveal the amino acid sequence of the protein. The isolated nucleic acid can then be used in routine cloning methods to produce the protein recombinantly. For example, the DNA encoding the protein may be inserted into a standard cloning vector. The vector can then be used to transform a suitable host, such as bacteria, e.g., *E. coli*. The host could then produce the protein, which can then be isolated. Techniques for primer synthesis, cloning, stringent conditions, and recombinant expression are described in B. Perbal, *A Practical Guide to Molecular Cloning*, Second Edition, John Wiley and Sons, 1988 and *Current Protocols in Molecular Biology*, F. M. Ausubel et al, Eds, Volumes 1–3, John Wiley and Sons, 119–1998, both of which are incorporated herein by reference.

EXAMPLES

Example 1

Analysis of a Protein Mixture

A standard protein mixture is used as the background matrix for this Example. The object of this Example is to detect mixtures that differ by the presence or absence of one or two individual proteins. Accordingly, a commercially produced mixture of protein molecular weight standards containing the proteins listed in Table 1 below is used.

| Matrix proteins | Molecular Weight | Number of Peptides |
| --- | --- | --- |
| Lysozyme, hen egg white | 16,238 | 3 |
| Trypsin inhibitor, soybean | 20,040 | 2 |
| Carbonic anhydrase, bovine | 28,982 | 4 |
| Ovalbumin, hen egg white | 42,882 | 12 |
| Serum albumin, bovine | 69,294 | 5 |
| Phosphorylase B, rabbit | 97,316 | 19 |
| Apomyoglobin, horse | 16,952 | 3 |
| β-Galactosidase, *E. coli* | 116,484 | 21 |

The proteins listed above are representative examples, and several similar mixtures are commercially available. If the mixture described above in the Table is used, the background matrix of CNBr peptides contains 45 peptides.

This mixture is divided into aliquots, to which known amounts of a specific protein is added. Thus, in one test experiment, sample A contains the matrix proteins, whereas sample B contains the matrix proteins plus apomyoglobin. The samples contain approximately equimolar amounts of both the matrix proteins and apomyoglobin. *E. coli* β-galactosidase is also used as a test protein. This protein is approximately 10-fold greater molecular weight than apomyoglobin and would thus test the ability to observe two proteins of dramatically different molecular weight. In subsequent experiments, a series of A/B samples, in which the A sample had the matrix proteins and a fixed amount of either apomyoglobin or β-galactosidase and the B sample had different amounts of the same protein, is prepared. The ratios would be varied from 1:0.1 to 10:1 in approximately 4–5 increments.

To confirm the identities of the differentially expressed CNBr peptides as apomyoglobin and β-galactosidase, HPLC peaks corresponding to the CNBr peptides are isolated, subjected to additional tryptic digestion, followed by ESI-MS-MS analysis. Peptide sequences are matched to protein sequence databases with SEQUEST and "hits' are confirmed by manual inspection of the MS-MS spectra for the tryptic peptides.

Example 2

Analysis of Differential Protein Expression at the Cellular Level

Samples

A human keratinocyte cell line (HaCaT) stably transfected with a neomycin resistance gene (pSV2 neo) and an AP-1-luciferase reporter gene is compared with untransfected HaCaT cells. The objective of this analysis is detecting the presence of the aminoglycoside phosphotransferase (APH (3')II) that confers neomycin resistance. Cell material is isolated from culture plates by scraping with a rubber policeman and then cellular proteins are extracted as described above.

Protein Digestion

CNBr cleavage of proteins is accomplished by dissolving the protein samples in 70% formic acid containing a 50-fold molar excess of CNB and incubating the samples in the dark at 25° C. for 12 to 24 hr. BSA cleavage is used for quality control. A similar digestion protocol involving the use of 50% trifluoroacetic acid can also be used.

The efficiency of cleavage by CNBr is assessed by two methods. First, SDS-PAGE analysis of the protein mixtures is performed to assess progress the cleavage reactions. Gels will be silver stained to detect both precursor proteins and CNBr peptides. Second, HPLC-ESI-MS analyzes of the protein mixtures and the CNBr digests are conducted to confirm cleavage of the proteins to peptides and to confirm that the peptides generated are those expected based on the cleavage specificity of CNBr.

Peptide Labeling and Assessment of Labeling Chemistry

Labeling reactions with the Cy dyes or Alexa dyes are conducted in aqueous sodium bicarbonate buffer at pH 9. Amine-containing buffers (e.g., Tris) are avoided. A gel filtration step may optionally be performed to remove unreacted dye. If a separation step is needed, a gel filtration with a low molecular weight cutoff gel (e.g., Biogel P10). Solvent extraction (e.g., with ethyl acetate) or solid phase batch cleanup may also be used.

Labeling efficiency is assessed by ESI-MS flow injection analysis of dye-treated peptide mixtures.

Detection of Labeled Peptides

A Thermo Separations Products quaternary HPLC system equipped with a variable wavelength detector and dual fluorescence detectors, computer, software, is used. The solvent delivery system is compatible with standard flow capabilities (0.1–2.0 mL min$^{-1}$) and can be adapted with the aid of a flow splitter to low-flow HPLC (1–50 μL min$^{-1}$). PEEK tubing is used for the entire system to minimize sample loss by nonspecific adherence to stainless steel. The system is under complete computer control and signals from the two fluorescence detectors can be processed simultaneously by the data system. A Vydac 238 TP-51 monomeric, 5 μm, 250×250×1 mm C-18 column is used. Alternatively, a C-8 or C-4 column may be used for these separations. N-Terminally labeled peptides are eluted with a linear gradient of 0.1% trifluoroacetic acid/acetonitrile.

Numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of detecting peptide fragments of at least one protein that is differentially present in biological samples, comprising the sequential steps of:
   digesting the protein in a plurality of biological samples to produce peptides in each sample;
   labeling the peptides;
   combining the samples;
   separating the peptides in the samples; and
   identifying the peptides that are differentially present in the samples;
   isolating at least a portion of the peptides that are differentially present in the samples; and
   determining the amino acid sequence of the isolated peptides.

2. The method of claim 1, wherein said labeling comprises labeling the peptides in each sample with a different labeling group.

3. The method of claim 2, wherein each labeling group is flourescent group and each flourescent group has a different flourescent emission wavelength.

4. The method of claim 3, wherein the labeled peptides are separated by high performance liquid chromatography.

5. The method of claim 4, wherein the labeled peptides are detected during the separation by simultaneous multichannel fluorescence emission detection.

6. The method of claim 5, wherein said plurality of biological samples is two samples.

7. The method of claim 1, wherein said plurality of biological samples is two samples.

8. The method of claim 1, wherein the peptides are separated by capillary electrophoresis or isoelectric focusing.

9. A method of identifying at least one protein that is differentially present in biological samples, comprising the sequential steps of:
   digesting the protein in a plurality of biological samples to produce peptides in each sample;
   separating the peptides in the samples; and
   identifying the peptides that are differentially present in the samples;
   determining the amino acid sequence of at least a portion of the peptide fragments that are differentially present in the samples; and
   correlating the amino acid sequences of the peptide fragments with the identity of at least one protein that is differentially present in the samples.

10. The method of claim 9, wherein said correlating comprising searching a sequence database for at least one protein sequence that contain the amino acid sequence of the peptide fragments as subsequences therein.

11. The method of claim 9, further comprising labeling the peptides prior to said separating.

12. The method of claim 11, further comprising combining the labeled peptides prior to said separating.

13. The method of claim 12, wherein said labeling comprises labeling the peptides in each sample with a different labeling group.

14. The method of claim 13, wherein each labeling group is flourescent group and each flourescent group has a different flourescent emission wavelength.

15. The method of claim 13, wherein the labeled peptides are separated by high performance liquid chromatography.

16. The method of claim 15, wherein the labeled peptides are detected during the separation by simultaneous multichannel fluorescence emission detection.

17. The method of claim 16, wherein said plurality of biological samples is two samples.

18. The method of claim 9, further comprising, prior to said determining, isolating at least a portion of the peptides that are differentially present in the samples.

19. The method of claim 11, further comprising combining the samples subsequent to said labeling and prior to said separating.

20. The method of claim 9, wherein said plurality of biological samples is two samples.

21. The method of claim 9, wherein the peptides are separated by capillary electrophoresis or isoelectric focusing.

22. The method of claim 9, wherein said correlating comprises:
   synthesizing an oligonucleotide probe based on the amino acid sequence of at least one peptide fragment, or a sub-fragment thereof, that is differentially present in the samples;
   hybridizing the oligonucleotide probe to nucleic acid from the sample under stringent conditions to identify nucleic acid in the sample which codes for the peptide fragment or sub-fragment thereof;
   determining the sequence of the hybridized nucleic acid; and
   determining the amino acid sequence encoded by the hybridized nucleic acid.

* * * * *